(12) United States Patent
Nalawade et al.

(10) Patent No.: US 12,605,533 B2
(45) Date of Patent: Apr. 21, 2026

(54) DISINFECTING ASSEMBLY FOR A PREFILLED SYRINGE AND SYRINGE INCLUDING SUCH AN ASSEMBLY

(71) Applicant: Becton, Dickinson and Company, Franklin Lakes, NJ (US)

(72) Inventors: Praveen Nalawade, Belagavi (IN); Shishir Prasad, Ramsey, NJ (US); Manish Kumar, Bengaluru (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 718 days.

(21) Appl. No.: 18/071,072

(22) Filed: Nov. 29, 2022

(65) Prior Publication Data

US 2024/0173536 A1    May 30, 2024

(51) Int. Cl.
*A61M 39/16*        (2006.01)

(52) U.S. Cl.
CPC ........ *A61M 39/162* (2013.01); *A61M 39/165* (2013.01)

(58) Field of Classification Search
CPC .. A61M 39/162; A61M 39/165; A61M 39/16; A61M 39/20
See application file for complete search history.

(56) References Cited

U.S. PATENT DOCUMENTS

| | | | | |
|---|---|---|---|---|
| 8,647,326 | B2 * | 2/2014 | Solomon ............. | A61M 39/162 604/533 |
| 8,671,496 | B2 | 3/2014 | Vaillancourt et al. | |
| 8,696,820 | B2 | 4/2014 | Vaillancourt et al. | |
| 8,740,864 | B2 | 6/2014 | Hoang et al. | |
| 9,039,989 | B2 | 5/2015 | Liu et al. | |
| 9,283,369 | B2 | 3/2016 | Ma et al. | |
| 9,399,125 | B2 * | 7/2016 | Burkholz ............ | A61M 39/162 |
| 9,480,833 | B2 | 11/2016 | Hoang et al. | |
| 9,700,710 | B2 * | 7/2017 | Anderson ............. | A61M 39/16 |
| D834,187 | S | 11/2018 | Ryan | |
| 10,166,381 | B2 * | 1/2019 | Gardner .............. | A61M 39/162 |
| 10,376,686 | B2 | 8/2019 | Burkholz et al. | |
| 10,413,716 | B2 | 9/2019 | Sathe | |
| 11,083,883 | B2 | 8/2021 | Ryan et al. | |
| 11,273,298 | B2 | 3/2022 | Erekovcanski et al. | |
| 11,344,715 | B2 | 5/2022 | Erekovcanski et al. | |
| 11,389,636 | B2 | 7/2022 | Coyle | |

(Continued)

*Primary Examiner* — Bradley J Osinski
(74) *Attorney, Agent, or Firm* — Servilla Whitney LLC

(57)            ABSTRACT

A disinfecting assembly for a prefilled flushing syringe. The disinfecting assembly includes a scrubbing cap and a disinfecting cap. The scrubbing cap includes a chamber adapted to receive a needle-free connector of an intravenous (IV) catheter. A scrubber and a disinfectant are contained within the chamber of the scrubbing cap. The disinfecting cap includes a chamber adapted to receive the needle-free connector of the IV catheter. A compressible sponge and disinfectant are contained within the chamber. The disinfecting cap is removably connected to the scrubbing cap. A tip cap, adapted to connect to and cover a syringe tip of the syringe, extends from one of the disinfecting cap and the scrubbing cap or a housing connecting the disinfecting cap and the scrubbing cap. Also, a prefilled flushing syringe including the disinfecting assembly and a method of using the prefilled flushing syringe to disinfect a needle-free connector and catheter.

23 Claims, 12 Drawing Sheets

(56)        References Cited

U.S. PATENT DOCUMENTS

| | | |
|---|---|---|
| 2012/0042466 A1 | 2/2012 | Colantonio et al. |
| 2012/0302968 A1 | 11/2012 | Tennican |
| 2012/0302997 A1 | 11/2012 | Gardner et al. |
| 2013/0035667 A1 | 2/2013 | Anderson et al. |
| 2013/0178804 A1 | 7/2013 | Tennican |
| 2013/0197485 A1 | 8/2013 | Gardner et al. |
| 2013/0338644 A1 | 12/2013 | Solomon et al. |
| 2014/0135739 A1 | 5/2014 | Solomon et al. |
| 2015/0005699 A1 | 1/2015 | Burbank et al. |
| 2015/0086441 A1 | 3/2015 | She et al. |
| 2016/0106968 A1 | 4/2016 | Solomon et al. |
| 2016/0144118 A1 | 5/2016 | Solomon et al. |
| 2016/0310720 A1 | 10/2016 | Solomon et al. |
| 2018/0055962 A1 | 3/2018 | Drmanovic |
| 2018/0064604 A1 | 3/2018 | Drmanovic |
| 2018/0071508 A1 | 3/2018 | Drmanovic |
| 2018/0085568 A1 | 3/2018 | Drmanovic |
| 2018/0200500 A1 | 7/2018 | Ziebol et al. |
| 2018/0214242 A1 | 8/2018 | Davis et al. |
| 2018/0214684 A1 | 8/2018 | Avula et al. |
| 2018/0250194 A1 | 9/2018 | Drmanovic |
| 2018/0256804 A1 | 9/2018 | Burbank et al. |
| 2018/0256880 A1 | 9/2018 | Follman et al. |
| 2018/0256881 A1 | 9/2018 | Hitchcock et al. |
| 2018/0256883 A1 | 9/2018 | Follman et al. |
| 2018/0369562 A1 | 12/2018 | Gardner et al. |
| 2019/0038888 A1 | 2/2019 | Gardner |
| 2019/0076885 A1 | 3/2019 | Ryan et al. |
| 2019/0099593 A1 | 4/2019 | Avula et al. |
| 2019/0117332 A1 | 4/2019 | Davis et al. |
| 2019/0201681 A1 | 7/2019 | Ziebol et al. |
| 2019/0262525 A1 | 8/2019 | Wyeth et al. |
| 2019/0282795 A1 | 9/2019 | Fangrow |
| 2019/0351212 A1 | 11/2019 | Dudar et al. |
| 2020/0121858 A1 | 4/2020 | Anderson et al. |
| 2020/0139037 A1 | 5/2020 | Ziebol et al. |
| 2020/0155794 A1 | 5/2020 | Ziebol |
| 2020/0197686 A1 | 6/2020 | Anderson et al. |
| 2020/0238070 A1 | 7/2020 | Ryan |
| 2021/0001110 A1 | 1/2021 | Bedoe et al. |
| 2021/0008283 A1 | 1/2021 | San Solo et al. |
| 2021/0093791 A1 | 4/2021 | Anderson et al. |
| 2021/0275707 A1 | 9/2021 | Jiang et al. |
| 2021/0322749 A1 | 10/2021 | Rothenberg et al. |
| 2021/0322750 A1 | 10/2021 | Harandi et al. |
| 2021/0322751 A1 | 10/2021 | Jiang et al. |
| 2021/0322752 A1 | 10/2021 | Jiang et al. |

* cited by examiner

DISINFECTING ASSEMBLY FOR A PREFILLED SYRINGE AND SYRINGE INCLUDING SUCH AN ASSEMBLY

BACKGROUND OF THE INVENTION

Field of the Invention

The present invention is directed to a disinfecting assembly for a prefilled flushing syringe, more specifically, a disinfecting assembly comprising a scrubbing cap and a disinfecting cap, and a prefilled flushing syringe including the disinfecting assembly.

Description of Related Art

Intravascular (IV) catheter care and standards of practice usually recommend that flush procedures be performed after IV catheter placement, before fluid infusion, and before and after drug administration, blood sampling, transfusions, and parenteral nutrition. Such procedures are outlined, for example, in the INS 2021 Infusion Therapy Standards of Practice. The goal of these flush procedures is to confirm IV catheter patency, avoid drug incompatibilities, ensure complete drug dose administration, prevent thrombus formation, and minimize the risk of blood stream infections.

IV catheter-related bloodstream infections are common and are caused by bacteria, fungi, and other infectious agents in patients with indwelling IV catheters. These infections can result in significant illness, or even death, as well as, excess medical costs. Current recommended practice is for the medical practitioner to perform a stepwise disinfecting process any time the IV catheter is accessed. This process requires several steps, including cleaning/disinfecting the needle-free connector of the indwelling IV catheter before the start of the procedure, pre-flushing by injecting a flushing solution, for example, saline, into the needle-free connector and IV catheter before a medication push or fluid withdrawal through the needle-free connector and IV catheter, cleaning/disinfecting of the needle-free connector of the IV catheter after pre-flushing, performing the medication push or fluid withdrawal, cleaning/disinfecting of the needle-free connector of the IV catheter after the a medication push or fluid withdrawal, post-flushing by injecting a flushing solution into the needle-free connector and IV line, locking the IV catheter, cleaning/disinfecting of the needle-free connector of the IV catheter, and covering the needle-free connector of the IV catheter. Further, this procedure requires four disinfecting wipes, two flush syringes, one lock syringe, and one cap. This extensive procedure makes indwelling IV catheter care and IV catheter line maintenance a very burdensome and time consuming process. Additionally, all of the components are provided individually and must be collected by the medical practitioner before starting the procedure.

Thus, there is a need for an assembly that provides all of the necessary components in a single device to encourage medical practitioners to follow all of the necessary disinfecting steps and to reduce costs.

SUMMARY OF THE INVENTION

The present invention is directed to a disinfecting assembly for a prefilled flushing syringe. The disinfecting assembly comprises a scrubbing cap and a disinfecting cap. The scrubbing cap comprises an open proximal end, a closed distal end, and a sidewall extending from the open proximal end of the scrubbing cap to the closed distal end of the scrubbing cap, a chamber defined by the sidewall of the scrubbing cap together with the closed distal end of the scrubbing cap and sized and shaped to receive a needle-free connector of an intravenous (IV) catheter, and a scrubber and disinfectant contained within the chamber of the scrubbing cap. The disinfecting cap comprises an open proximal end, a closed distal end, and a sidewall extending from the open proximal end of the disinfecting cap to the closed distal end of the disinfecting cap, a chamber defined by the sidewall of the disinfecting cap together with the closed distal end of the disinfecting cap and sized and shaped to receive a needle-free connector of an intravenous catheter, and a compressible sponge and disinfectant contained with the chamber of the disinfecting cap. The disinfecting cap is removably connected to the scrubbing cap The scrubber may fill at least a portion of the chamber of the scrubbing cap. The scrubber may be saturated with the disinfectant and/or the scrubber may be fastened in a proximal portion of the chamber of the scrubbing cap, and the disinfectant is contained in a distal portion of the chamber of the scrubbing cap. The scrubber may be held in the proximal portion of the scrubbing cap by an interaction between a circumferential flange extending radially outward from the scrubber and a ledge extending radially inward from an inner surface of the sidewall of the scrubbing cap.

An outer diameter of a proximal portion of the scrubbing cap may be greater than an outer diameter of a distal portion of the scrubbing cap, and/or an inner diameter of the proximal portion of the scrubbing cap may be greater than an inner diameter of the distal portion of the scrubbing cap. The scrubber may be substantially contained in the proximal portion of the scrubbing cap.

The scrubber may have at least one slit and/or at least one recess in the proximal end of the scrubber, where the at least one slit and/or the at least one recess are adapted to receive the needle-free connector of an IV catheter when the needle-free connector is inserted into the scrubbing cap The open proximal end of the scrubbing cap may be sealed by a removable cover. The removable cover may be a film that is adhered to the open proximal end of the scrubbing cap. The removable cover may include a pull tab extending outwardly from a scaling portion of the removable cover. A circumferential flange may extend radially outward from the open proximal end of the scrubbing cap with the removable cover adhered to the circumferential flange.

The sponge may fill at least a portion of the cavity of the disinfecting cap. Threads may be provided in an inner surface of the sidewall of the disinfecting cap.

The open proximal end of the disinfecting cap may be sealed by a removable cover. The removable cover may be a film that is adhered to the open proximal end of the disinfecting cap. The removable cover may include a pull tab extending outwardly from a sealing portion of the removable cover. A circumferential flange may extend radially outward from the proximal end of the disinfecting cap with the removable cover adhered to the circumferential flange.

Protrusions may extend radially outward from an outer surface of the sidewall of the scrubbing cap to aid the user in gripping the scrubbing cap during removal of the removable cover and during the scrubbing of the needle-free connector and/or protrusions may extend radially outward from an outer surface of the sidewall of the disinfecting cap to aid the user in gripping the disinfecting cap during removal of the removable cover and during placement of the disinfecting cap on the needle-free connector.

The disinfecting assembly may further comprise a tip cap extending distally from the closed distal end of one of the disinfecting cap and the scrubbing cap and adapted to connect to and cover a syringe tip of the prefilled syringe. The tip cap may comprise a closed proximal end, an open distal end, and a sidewall extending from the closed proximal end to the open distal end, and the sidewall of the tip cap together with the closed proximal end of the tip cap may define a cavity sized and shaped to receive and cover the syringe tip of the syringe. The sidewall of the tip cap may be provided with external threads adapted to engage internal threads of a luer lock surrounding the syringe tip.

The closed distal end of one of the disinfecting cap and the scrubbing cap may be bonded to the open proximal end of the other of the disinfecting cap and the scrubbing cap. The open proximal end of one of the disinfecting cap and the scrubbing cap may include a retaining portion comprising a circumferential flange extending radially outward from the open proximal end of the one of the disinfecting cap and the scrubbing cap and a retaining sidewall extending distally from an outer perimeter of the circumferential flange. The closed distal end of the other of the disinfecting cap and the scrubbing cap is received in the retaining portion.

One of the disinfecting cap and the scrubbing cap may be attached to the other of the disinfecting cap and the scrubbing cap via a removable disc. The open proximal end of the one of the disinfecting cap and the scrubbing cap may have a retaining portion to which the disc is removably attached. The retaining portion may comprise a circumferential flange extending radially outward from the open proximal end of the one of the disinfecting cap and the scrubbing cap and a retaining sidewall extending distally from an outer perimeter of the circumferential flange, and the disc may rest on the circumferential flange of the retaining portion and be held in place by a retaining flange extending radially inward around at least a portion of the proximal end of the retaining sidewall, such that the disc is in a snap-fit engagement with the one of the disinfecting cap and the scrubbing cap. A circumferential groove may be provided in an outer surface of the sidewall of the other of the disinfecting cap and the scrubbing cap at the closed distal end of the other of the disinfecting cap and the scrubbing cap, a flexible, annular protrusion extends proximally from the disc, and the annular protrusion is received in the circumferential groove in a snap-fit engagement.

The scrubbing cap and the disinfecting may be connected by a housing. The housing may comprise an open proximal end, a closed distal end, and a sidewall extending from the open proximal end to the closed distal end, where the sidewall of the housing together with the closed distal end of the housing define a cavity sized and shaped to receive one of the disinfecting cap and the scrubbing cap and at least a portion of the other of the disinfecting cap and the scrubbing cap.

A tip cap adapted to connect to and cover the syringe tip of the prefilled syringe may extend distally from the closed distal end of the housing. The tip cap may comprise a closed proximal end, an open distal end, and a sidewall extending from the closed proximal end to the open distal end, where the sidewall of the tip cap together with the closed proximal end of the tip cap define a cavity sized and shaped to receive and cover the syringe tip of the syringe.

The housing may comprise a body portion and a retaining portion, and one of the disinfecting cap and the scrubbing cap may be connected to the retaining portion of the housing. An inner diameter of the retaining portion of the housing may be greater than an inner diameter of the body portion of the housing and/or an outer diameter of the retaining portion of the housing may be greater than an outer diameter of the body of the housing.

The sidewall of the housing may include a recess through which a pull tab of a removable cover of one of the disinfecting cap and the scrubbing cap extends.

One of the disinfecting cap and the scrubbing cap may be positioned in the cavity of the housing, such that the closed distal end of the one of the disinfecting cap and the scrubbing cap rests on the closed distal end of the housing, a closed distal end of the other of the disinfecting cap and the scrubbing cap is received in the cavity of the housing and is removably connected to the housing, the open proximal end of the one of the disinfecting cap and the scrubbing cap is adjacent the closed distal end of the other of the disinfecting cap and the scrubbing cap, and the open proximal end of the other of the disinfecting cap and the scrubbing cap extends proximally from the housing.

A flexible, annular protrusion may extend radially inward from an inner surface of the sidewall of the housing, a circumferential groove may be provided in the outer surface of the sidewall of one of the disinfecting cap and the scrubbing cap, and the annular protrusion of the housing may be removably received in the circumferential groove in a snap-fit engagement to connect the one of the disinfecting cap and the scrubbing cap to the housing.

Alternatively, a circumferential groove may be provided in an inner surface of the sidewall of the housing, a flexible, annular protrusion may extend radially outward from an outer surface of the sidewall of one of the disinfecting cap and the scrubbing cap, and the annular protrusion may be removably received in the circumferential groove in a snap-fit engagement to connect the one of the disinfecting cap and the scrubbing cap to the housing.

Alternatively, threads may be provided on an inner surface of the sidewall of the housing, a circumferential attachment flange may extend proximally from an outer surface of the sidewall of one of the disinfecting cap and the scrubbing cap, the threads may be provided on an outer surface of the attachment flange, and the threads on the outer surface of the attachment flange may engage the threads on the inner surface of the sidewall of the housing to attach the one of the disinfecting cap and the scrubbing cap to the housing.

The present invention is also directed to a prefilled flushing syringe comprising a syringe comprising a chamber having a syringe tip defining a lumen having an opening through which flushing solution may be expelled from the chamber and the disinfecting assembly discussed above, wherein the disinfecting assembly and the syringe are connected by an engagement provided between the tip cap and the syringe tip.

The present invention is also directed to a method of disinfecting an indwelling IV catheter. A prefilled flushing syringe with a disinfecting assembly, as discussed above, is provided. The disinfecting cap is disconnected from the scrubbing cap. The removable cover is removed from the scrubbing cap. The needle-free connector of the IV catheter is inserted into the chamber of the scrubbing cap. The needle-free connector is moved longitudinally and/or rotated with respect to the scrubber to scrub the needle-free connector and clean the needle-free connector with the disinfectant. Whichever of the disinfecting cap or the scrubbing cap that is connected to the syringe is disconnected from the syringe. The syringe is connected to the needle-free connector, and the needle-free connector and the IV catheter are flushed with the flushing solution. The syringe is disconnected from the needle-free connector. The needle-free connector is covered with the disinfecting cap.

Alternatively, a prefilled flushing syringe with a disinfecting assembly, as discussed above, is provided. The disinfecting cap or the scrubbing cap is disconnected from the housing. The removable cover is removed from the scrubbing cap. The needle-free connector of the IV catheter is inserted into the chamber of the scrubbing cap. The needle-free connector is moved longitudinally and/or rotated with respect to the scrubber to scrub the needle-free connector and clean the needle-free connector with the disinfectant. The housing is disconnected from the syringe. The syringe is connected to the needle-free connector, and the needle-free connector and the IV catheter are flushed with the flushing solution. The syringe is disconnected from the needle-free connector. The needle-free connector is covered with the disinfecting cap.

DESCRIPTION OF THE INVENTION

As used herein, any numerical values are expressed using a period as a decimal point and a comma as a thousand separator, for example, 1,234 would be one thousand two hundred thirty four, and 1.2 would be one and two tenths. Unless otherwise expressly specified, all numbers, such as those expressing values, amounts, ranges, amounts or percentages, may be read as if prefaced by the word "about", even if the term does not expressly appear. Any numerical range, recited herein, is intended to include all sub-ranges subsumed therein. For example, a range of "1 to 10" is intended to include any and all sub-ranges between and including the recited minimum value of 1 and the recited maximum value of 10, that is, all sub-ranges beginning with a minimum value equal to or greater than 1 and ending with a maximum value equal to or less than 10, and all sub-ranges in between, e.g., 1 to 6.3, or 5.5 to 10, or 2.7 to 6.1. Plural encompasses singular and vice versa. When ranges are given, any endpoints of those ranges and/or numbers within those ranges can be combined within the scope of the present invention. "Including", "such as", "for example", and like terms mean "including/such as/for example but not limited to".

For purposes of the description hereinafter, spatial orientation terms, for example, "upper", "lower", "right", "left", "vertical", "horizontal", "top", "bottom", "lateral", "longitudinal", "proximal", "distal", and derivatives thereof, relate to the invention as it is oriented in the accompanying drawings, figures, or otherwise described in the following detailed description. However, it is to be understood that the embodiments described hereinafter may assume many alternative variations and configurations. It is also to be understood that the specific components, devices, features, and operational sequences illustrated in the accompanying drawings, figures, or otherwise described herein, are simply exemplary and should not be considered as limiting.

As referred to herein, "proximal" refers to the end of the device and the direction indicated by the arrow "P" in the figures, and "distal" refers to the end of the device and the direction indicated by the arrow "D" in the figures.

The present invention is directed to a disinfecting assembly 10*a*-10*h* for a prefilled flushing syringe and a prefilled flushing syringe 12, including the disinfecting assembly 10*a*-10*h*.

Figure 3:
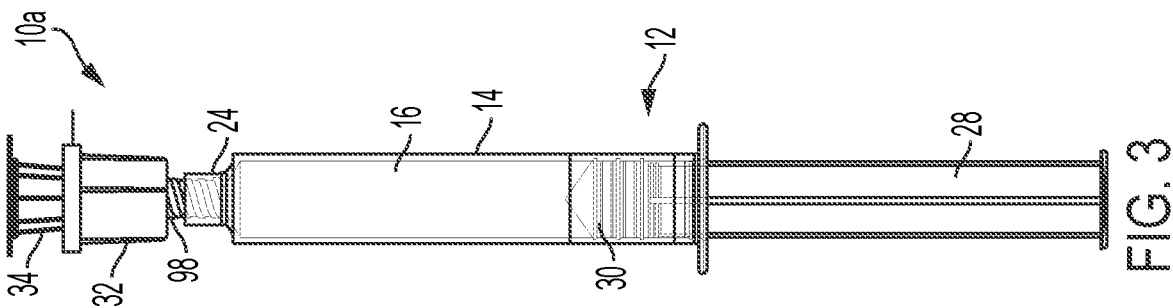
FIG. 3 is a side view of a syringe including the disinfecting assembly of FIG. 1 according to the invention.
Figure 7:
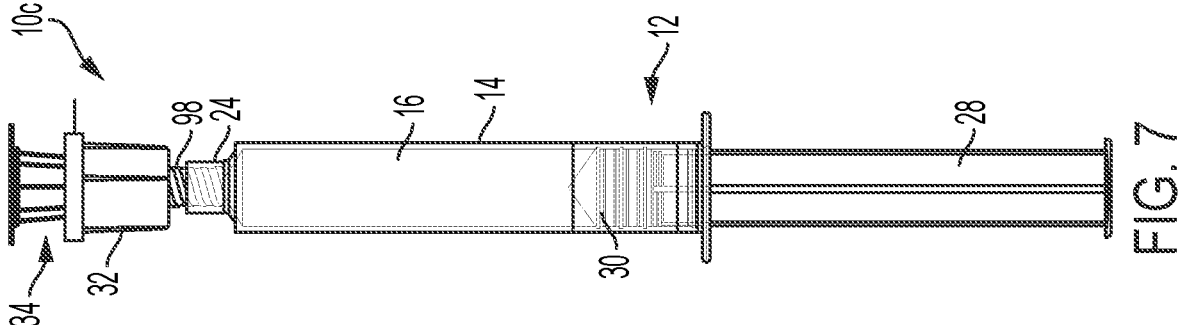
FIG. 7 is a side view of a syringe including the disinfecting assembly of FIG. 6 according to the invention.
Figure 12:
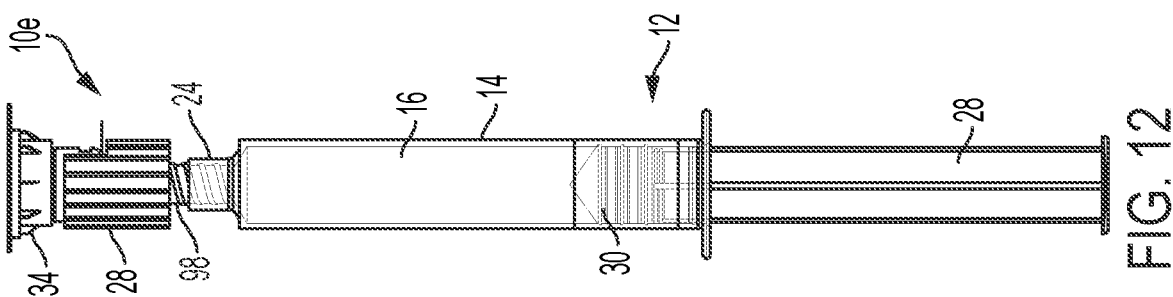
FIG. 12 is a side view of a syringe including the disinfecting assembly of FIG. 10 according to the invention.
Figure 16:
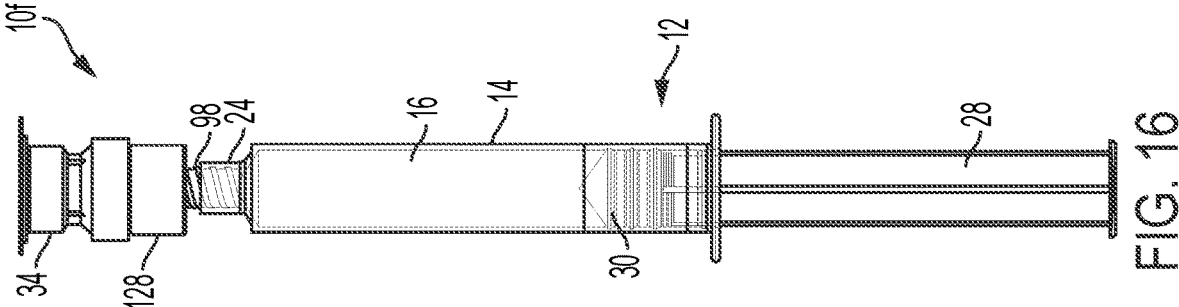
FIG. 16 is a side view of a syringe including the disinfecting assembly of FIG. 15 according to the invention.

The disinfecting assembly 10*a*-10*h* is used with standard prefilled syringes. As shown in FIGS. 3, 7, 12, and 16, the syringe 12 comprises a syringe body 14 defining a chamber 16 for holding a flushing solution and having a syringe tip 18 having lumen 20 with an opening 22 through which the flushing solution can be expelled from the chamber 16. The syringe tip 18 may be, for example, a male luer taper and may be surrounded by a threaded luer lock 24. The syringe tip 18 may be removably attached to a needle-free connector 26 of an indwelling intravenous (IV) catheter. A plunger rod 28 attached to a stopper 30 disposed within the chamber 16 of the syringe body 14 is movable with respect to the syringe body 14, such that a distal force applied to the plunger rod 28, while holding the syringe body 14 stationary, causes the stopper attached thereto to be displaced in a distal direction within the chamber 16 of the syringe body 14, thereby expelling the flushing solution through the opening 22 of the syringe tip 18, through the needle-free connector 26, and into the indwelling IV catheter.

Figure 2:
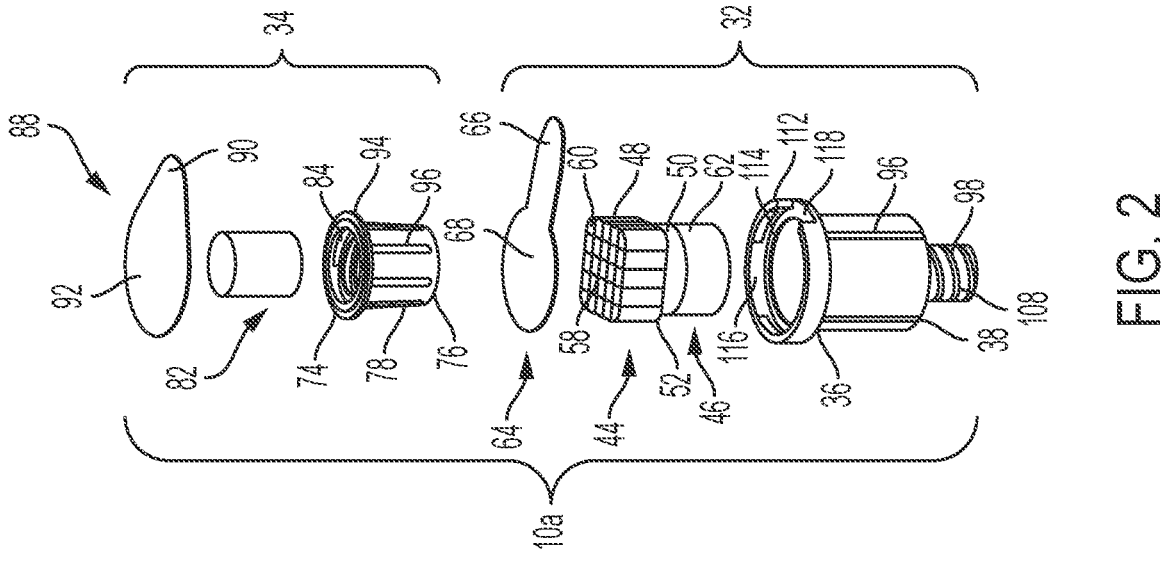
FIG. 2 is an exploded side perspective view of the disinfecting assembly of FIG. 1.
Figure 1:
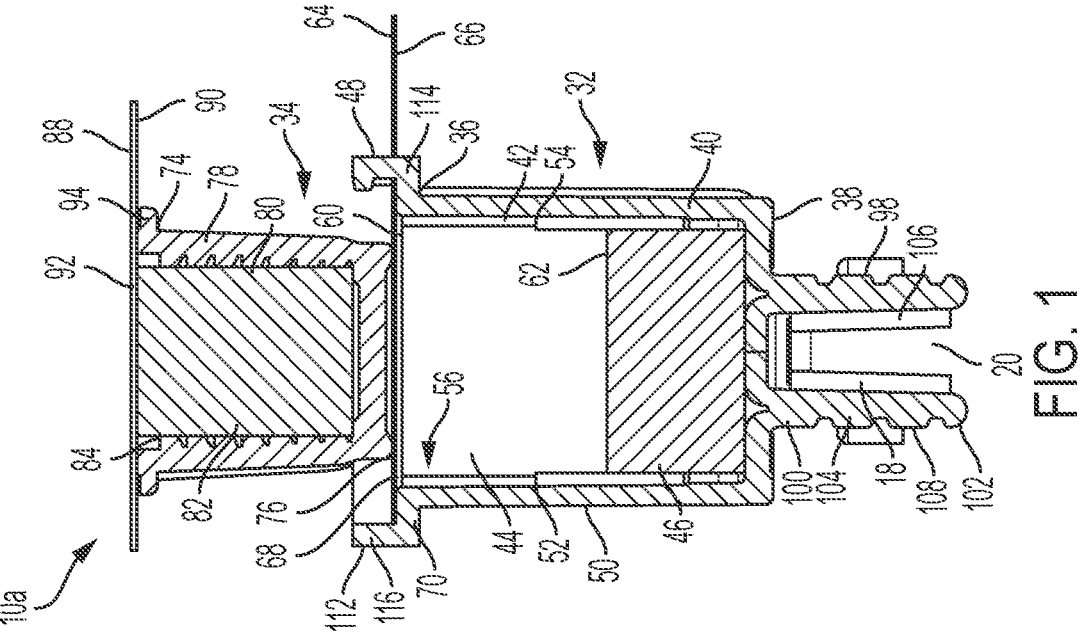
FIG. 1 is a cross-sectional view of a first embodiment of a disinfecting assembly according to the invention.
Figure 4:
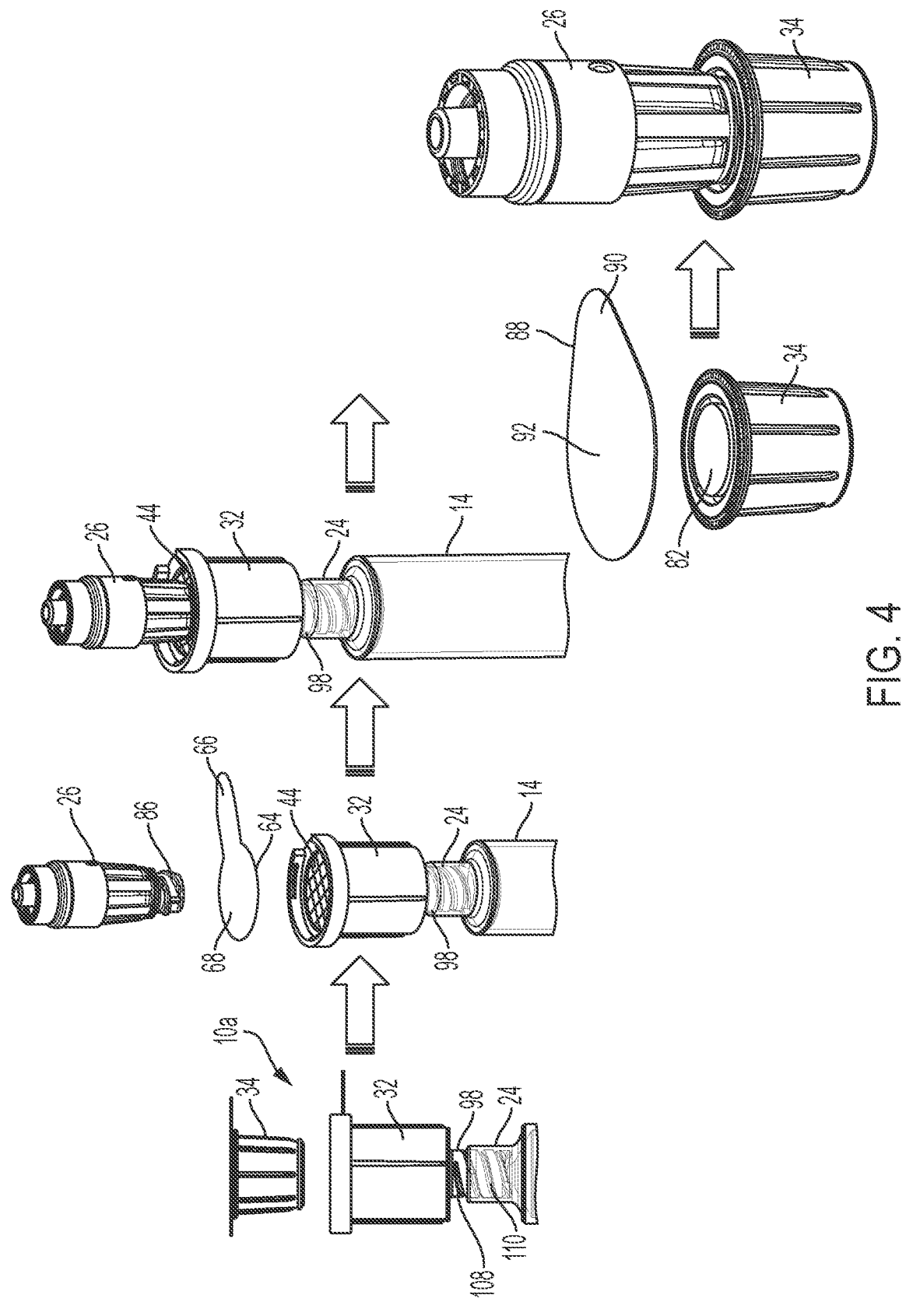
FIG. 4 is a schematic showing the disinfecting assembly of FIG. 1 in use.
Figure 5:
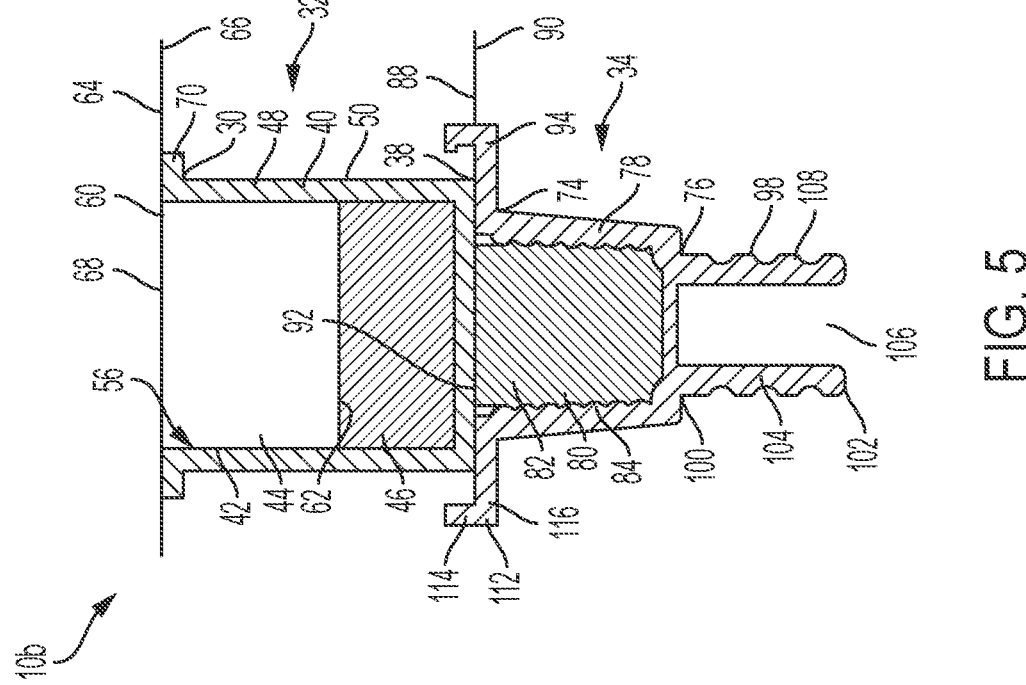
FIG. 5 is a cross-sectional view of a second embodiment of a disinfecting assembly according to the invention.
Figure 6:
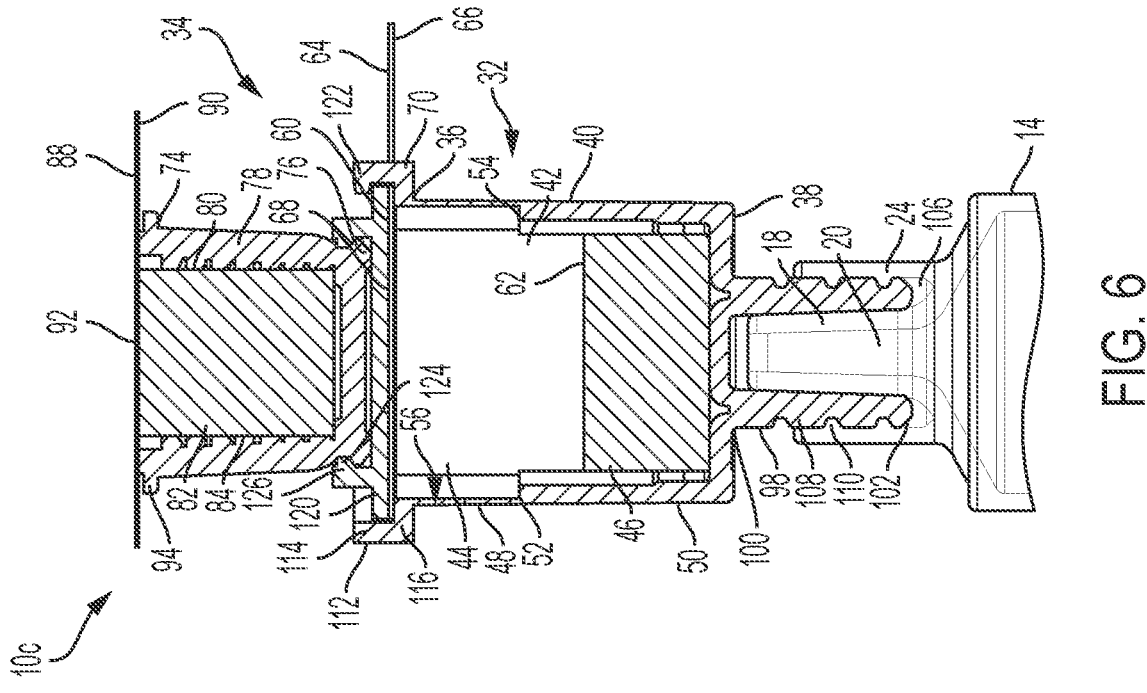
FIG. 6 is a cross-sectional view of a third embodiment of a disinfecting assembly according to the invention.
Figure 8:
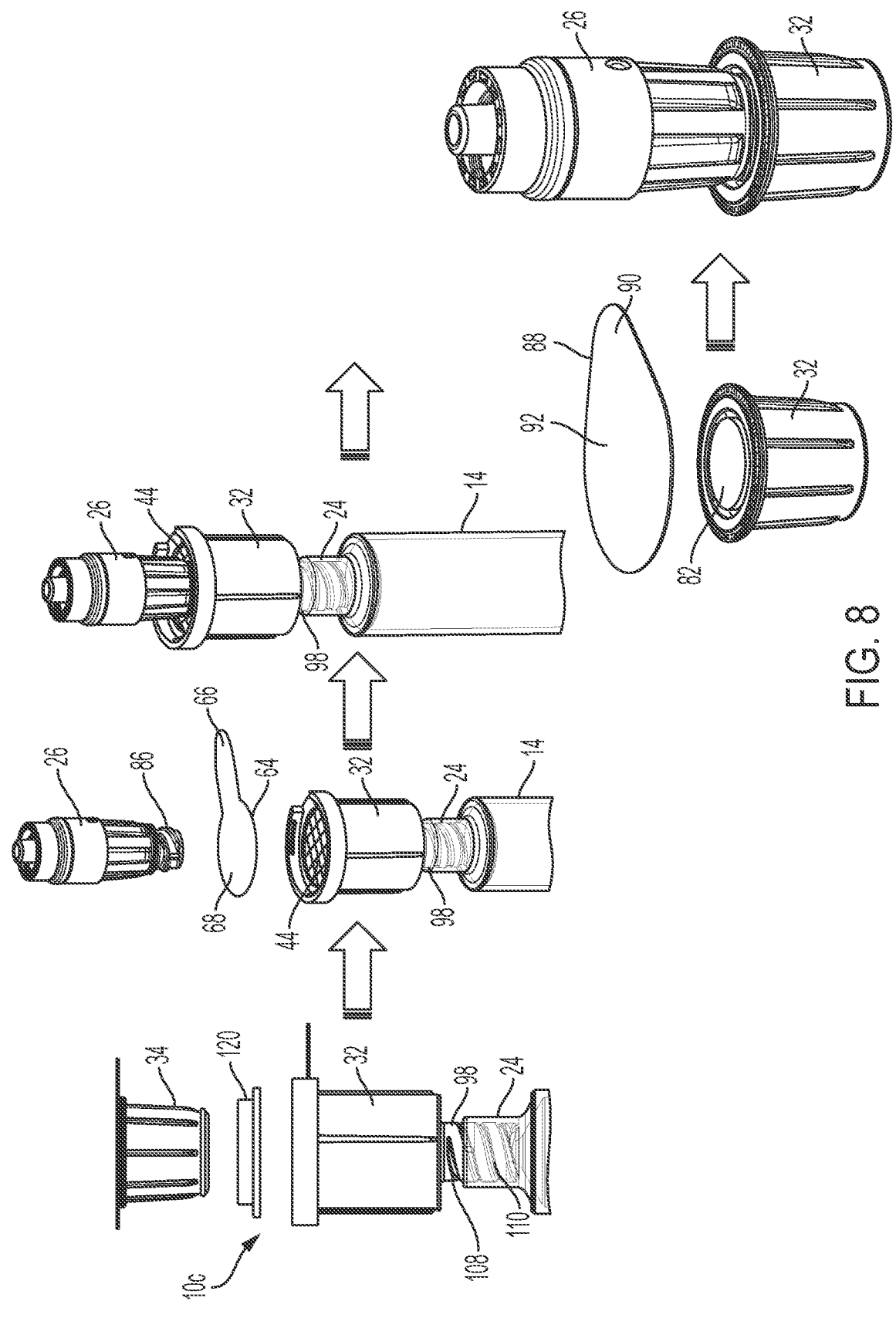
FIG. 8 is a schematic showing the disinfecting assembly of FIG. 6 in use.
Figure 9:
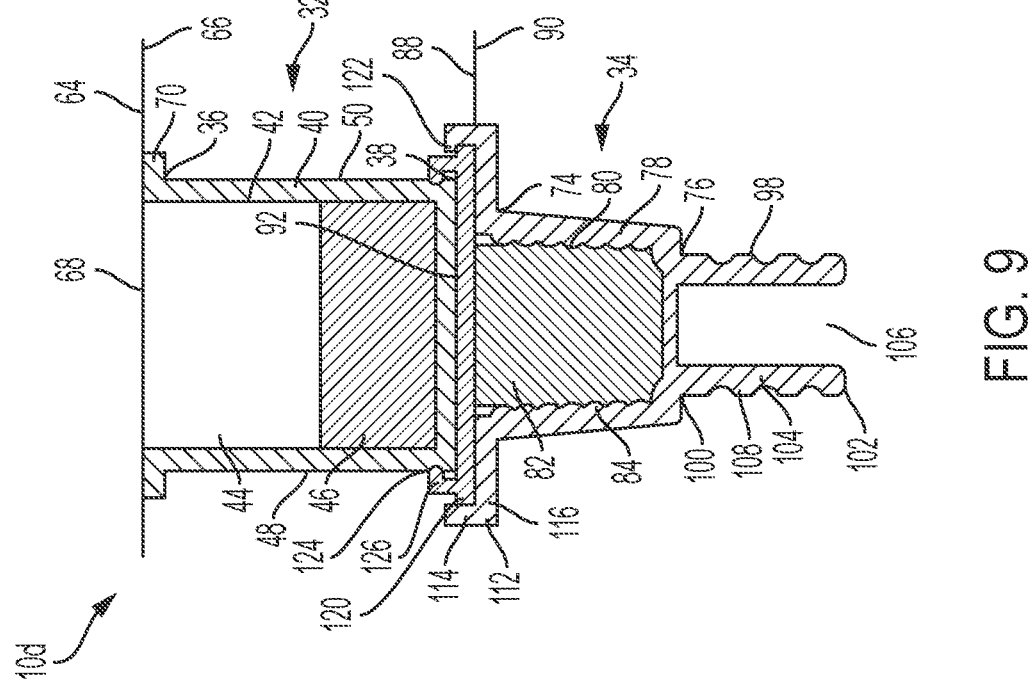
FIG. 9 is a cross-sectional view of a fourth embodiment of a disinfecting assembly according to the invention.
Figure 11:
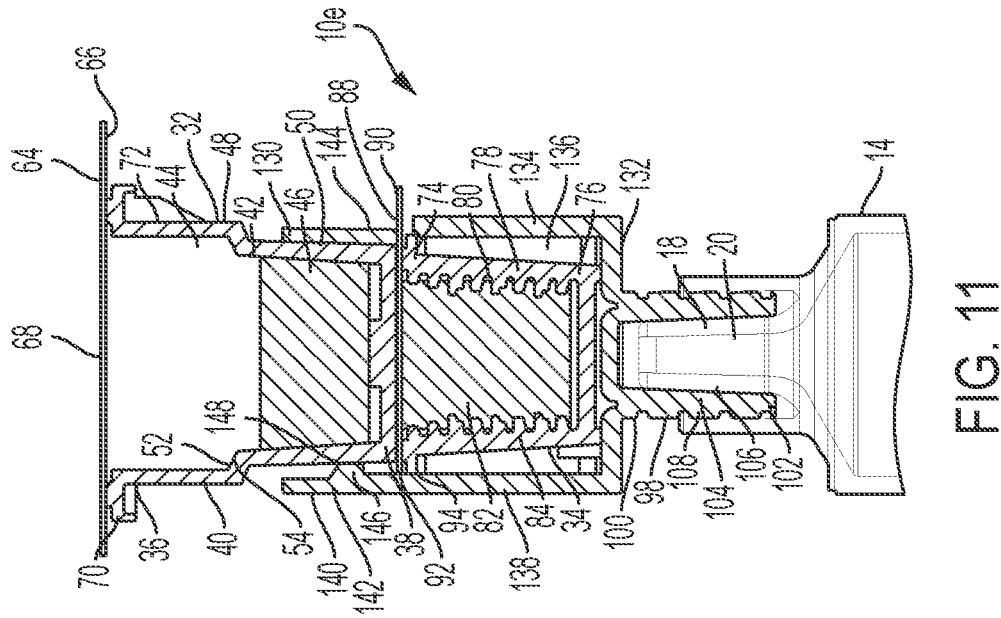
FIG. 11 is a cross-sectional view the disinfecting assembly of FIG. 10.
Figure 10:
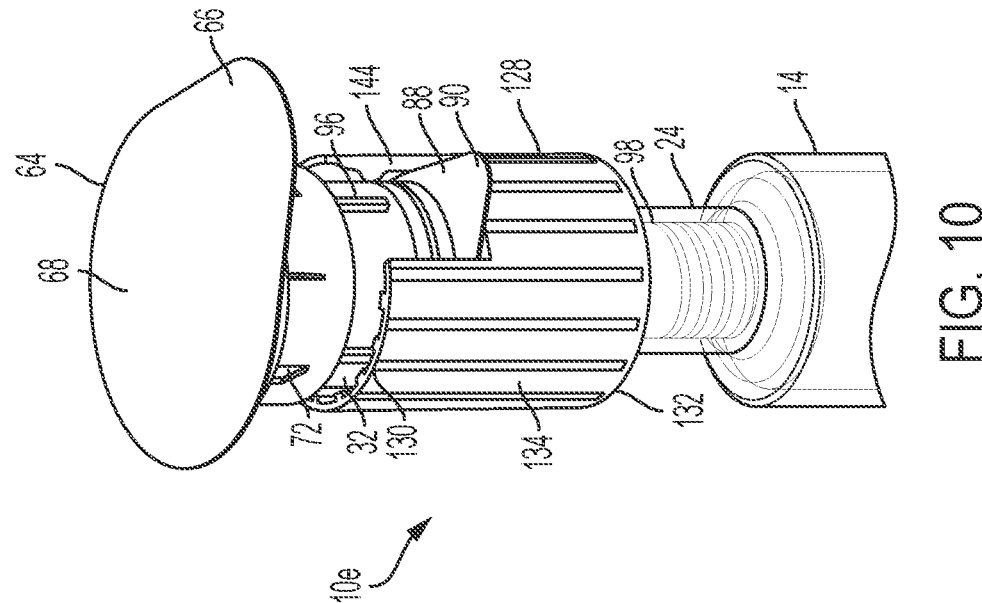
FIG. 10 is a side perspective view of a fifth embodiment of a disinfecting assembly according to the invention.
Figure 13:
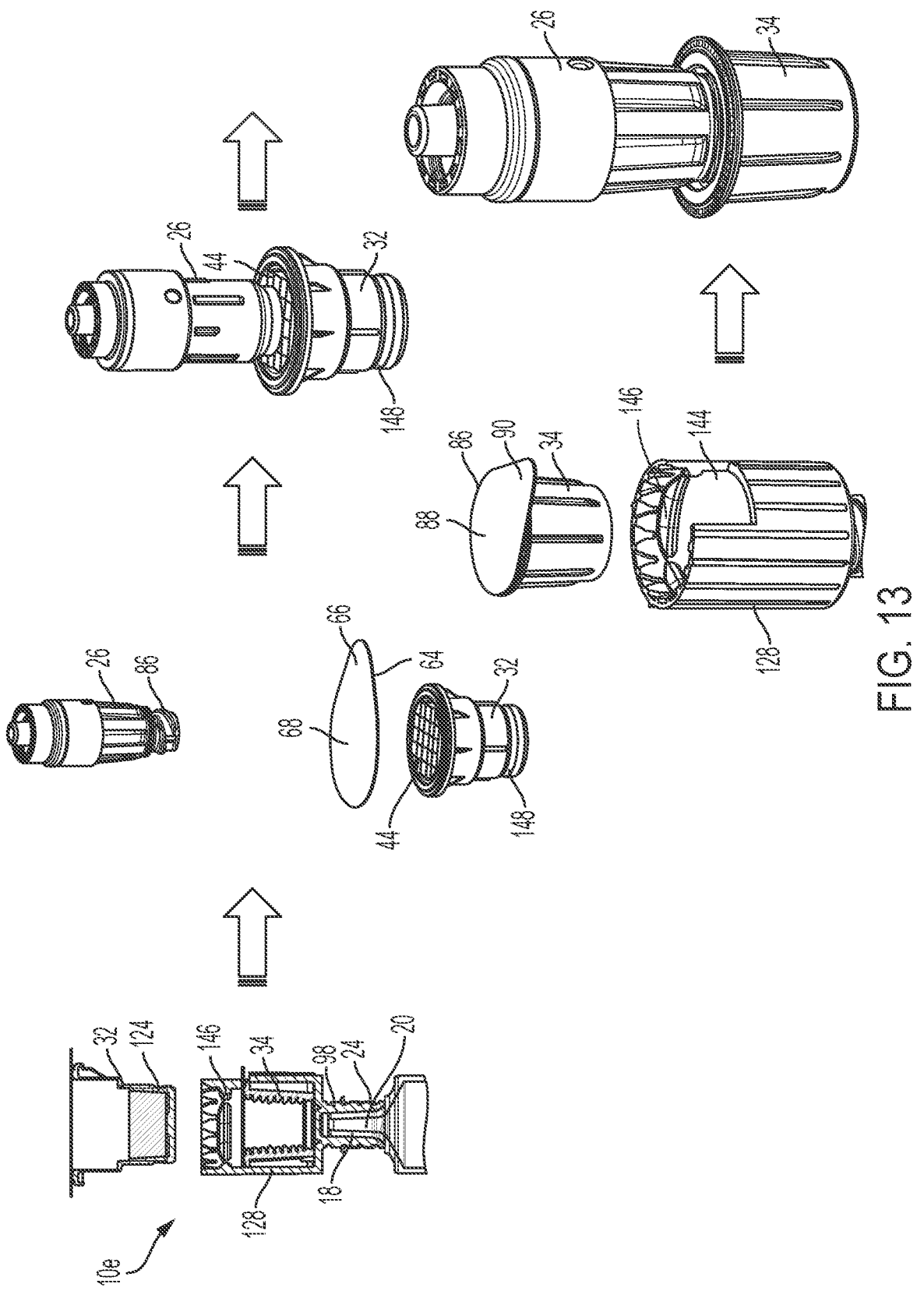
FIG. 13 is a schematic showing the disinfecting assembly of FIG. 10 in use.
Figure 14:
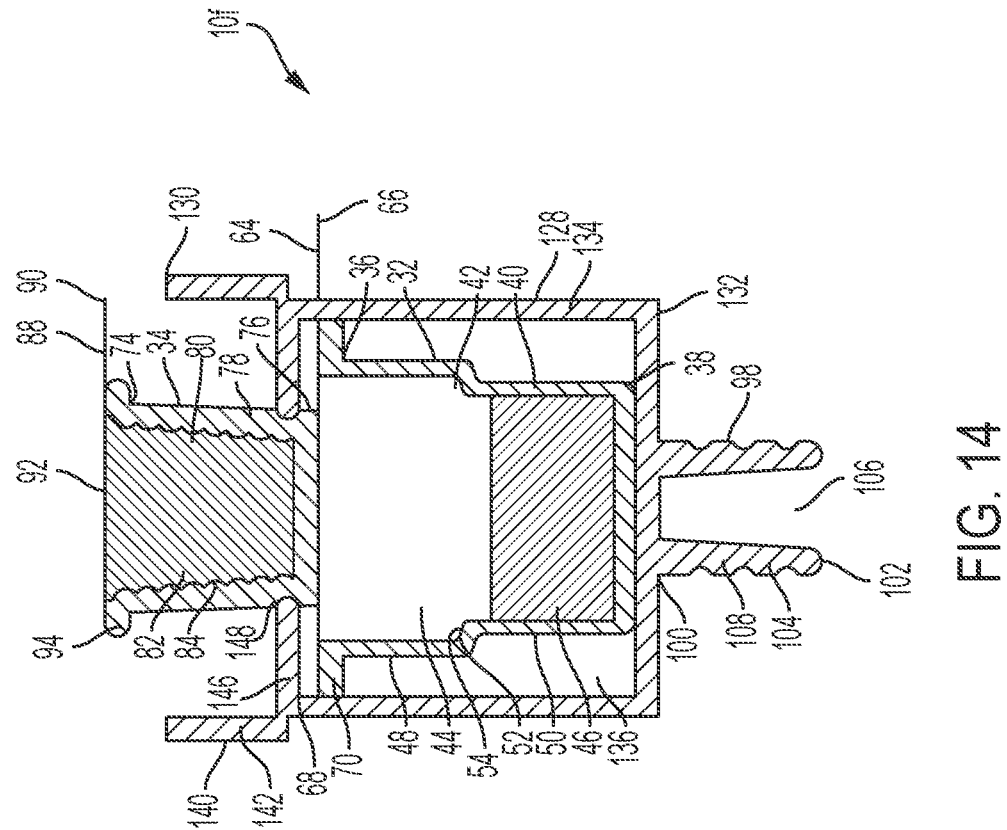
FIG. 14 is a cross-sectional view of a sixth embodiment of a disinfecting assembly according to the invention.
Figure 15:
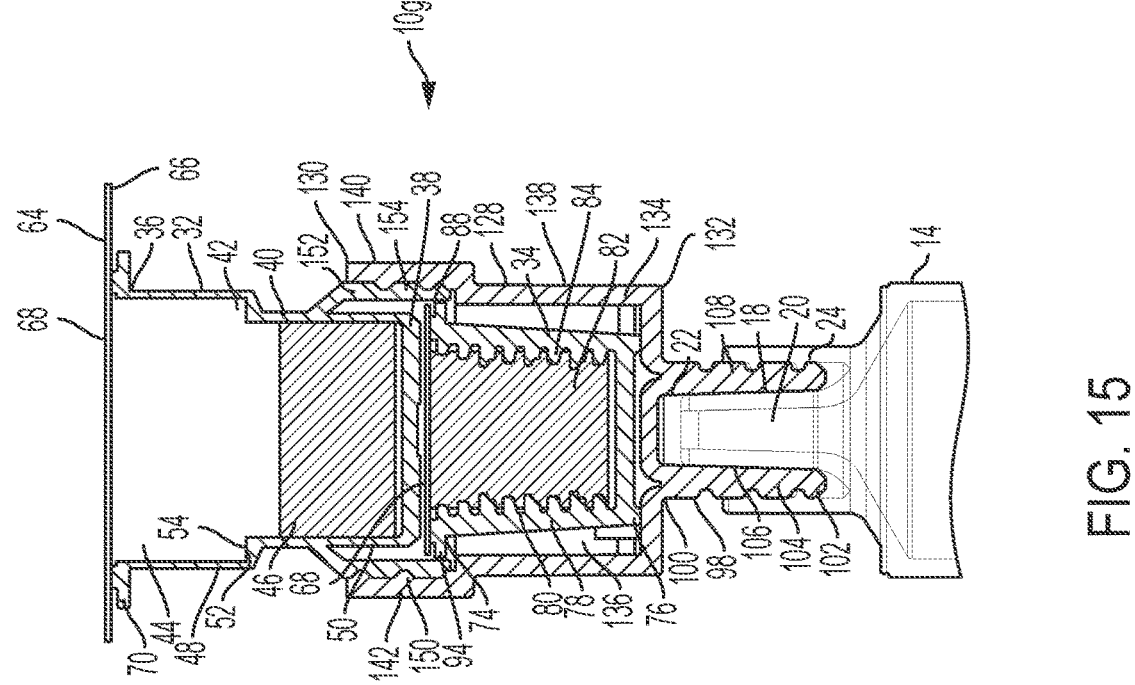
FIG. 15 is a cross-sectional view of a seventh embodiment of a disinfecting assembly according to the invention.
Figure 17:
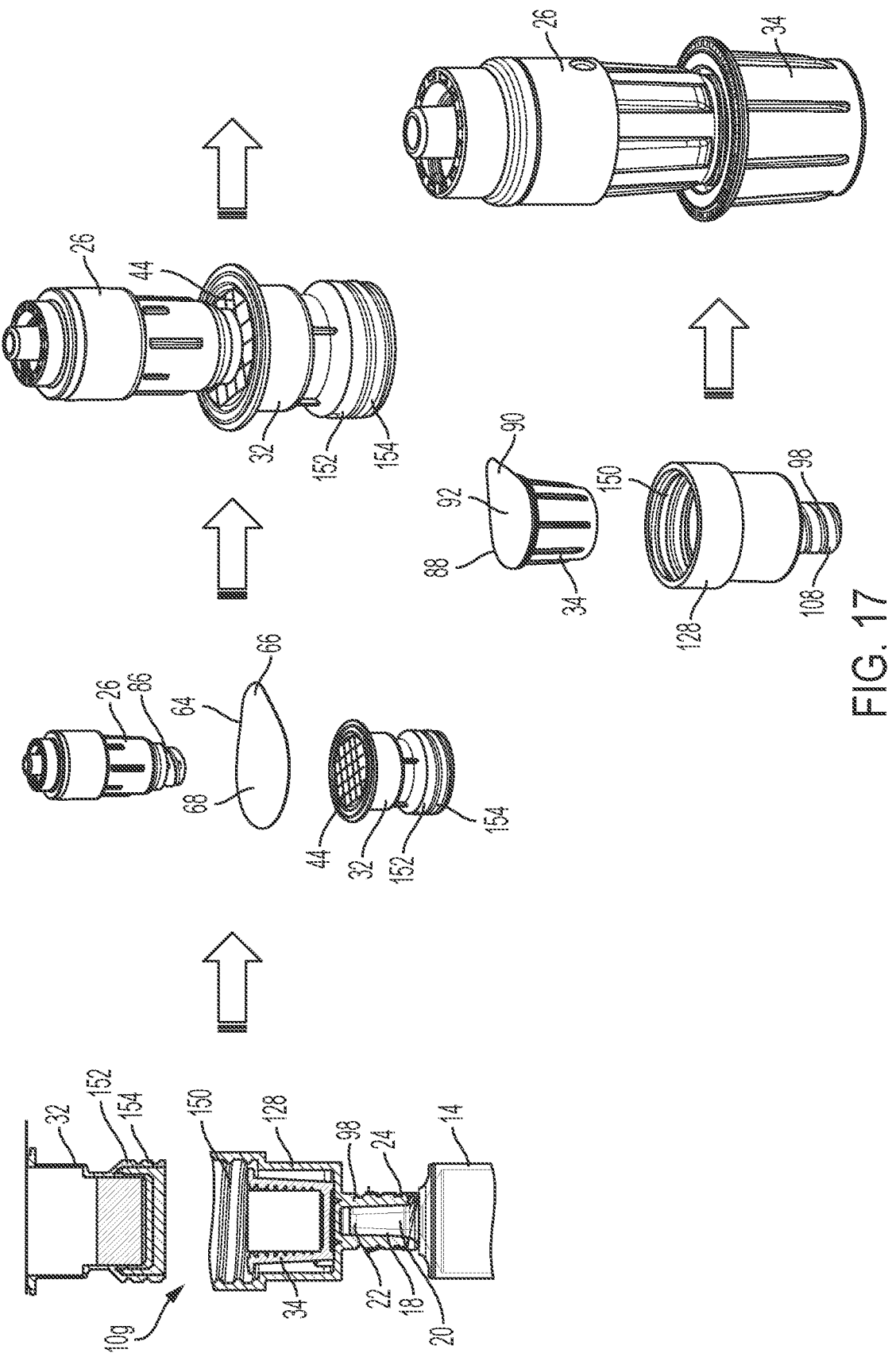
FIG. 17 is a schematic showing the disinfecting assembly of FIG. 15 in use.
Figure 18:
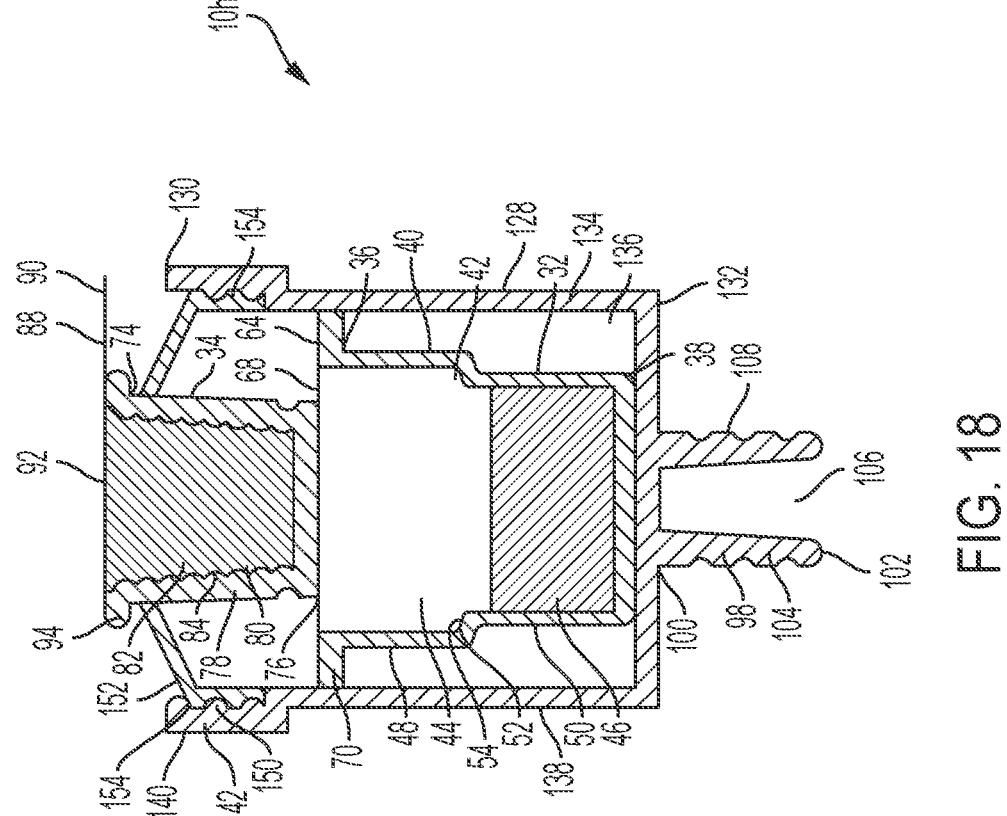
FIG. 18 is a cross-sectional view of an eighth embodiment of a disinfecting assembly according to the invention.

As shown in FIGS. 1-18, the disinfecting assembly 10*a*-10*h* comprises a scrubbing cap 32 and a disinfecting cap 34.

The scrubbing cap 32 comprises an open proximal end 36, a closed distal end 38, and a sidewall 40 extending from the open proximal end 36 to the closed distal end 38. The sidewall 40, together with the closed distal end 38, define a chamber 42 sized and shaped to receive the needle-free connector 26 of the indwelling IV catheter. The scrubbing cap 32 may be substantially cylindrical. A scrubber 44 and a disinfectant 46 are contained in the chamber 42 of the scrubbing cap 32. The scrubber 44 may be substantially cylindrical and may fill at least a portion of the chamber 42 of the scrubbing cap 32. The scrubber 44 may be made of a material that can be penetrated with the disinfectant 46. The scrubber 44 may be saturated with the disinfectant 46 and/or the scrubber 44 may be fastened in a proximal portion 48 of the scrubbing cap 32, and the disinfectant 46 may be contained in a distal portion 50 of the scrubbing cap 32. In some embodiments, the scrubber 44 may be held in the proximal portion 48 of the scrubbing cap 32 by the inter-action between a circumferential flange 52 extending radi-ally outward from the scrubber 44 and a ledge 54 extending radially inward from an inner surface 56 of the sidewall 40 of the scrubbing cap 32.

In some embodiments, the outer diameter of the proximal portion 48 of the scrubbing cap 32 may be greater than an outer diameter of the distal portion 50 of the scrubbing cap 32, and/or the inner diameter of the proximal portion 48 of the scrubbing cap 32 may be greater than an inner diameter of the distal portion 50 of the scrubbing cap 32. The scrubber 44 may be substantially contained in the proximal portion 48 of the scrubbing cap 32.

In some embodiments, the scrubber 44 may have at least one slit and/or at least one recess 58 in a proximal end 60 of the scrubber 44. The slit(s) and/or recess(es) 58 may be adapted to receive the needle-free connector 26 of the indwelling IV catheter when the needle-free connector 26 is inserted into the scrubbing cap 32. For example, the proxi-mal end 60 of the scrubber 44 may have slits 58 in the shape of a grid, may have slits 58 in the form of slices in the scrubber 44, or may have a recessed blind hole adapted to receive the needle free connector 26. The slit(s) and/or recess(es) 58 may extend partially through the scrubber 44 from the proximal end 60 of the scrubber 44 in a longitudinal direction of the scrubber 44 or may extend completely through the scrubber 44 from the proximal end 60 of the scrubber 44 to a distal end 62 of the scrubber 44 in a longitudinal direction of the scrubber 44. After insertion of the needle-free connector 26 into the scrubber 44, the needle-free connector 26 may be moved up and down in a longitudinal direction with respect to the scrubber 44 and/or rotated with respect to the scrubber 44 to disinfect the needle-free connector 26. If the scrubber 44 is fastened in the proximal portion 48 of the scrubbing cap 32 and the disinfectant 46 is contained in the distal portion 50 of the scrubbing cap 32, the needle-free connector 26 may be moved up and down in a longitudinal direction with respect to the scrubber 44, such that the needle-free connector 26 is alternately immersed in the disinfectant 46 and scrubbed by the scrubber 44.

The disinfectant 46 may be any suitable disinfecting liquid that has the ability to kill bacteria, fungus, viruses, and other infectious agents. For example, the disinfectant 46 may be isopropyl alcohol (IPA), chlorhexidine gluconate of appropriate proportion in IPA, or any other disinfectant suitable for effective microbial kill in medical applications.

The open proximal end 36 of the scrubbing cap 32 is sealed by a removable cover 64. The removable cover 64 may be a film that is adhered to the open proximal end 36 of the scrubbing cap 32. The removable cover 64 may include a pull tab 66 extending outwardly from a sealing portion 68 of the removable cover 64. In use, a medical practitioner can grasp the pull tab 66 to remove the remov-able cover 64 from the scrubbing cap 32. In some embodi-ments, a circumferential flange 70 may extend radially outward from the open proximal end 36 of the scrubbing cap 32, and the removable cover 64 may be adhered to the circumferential flange 70. In some embodiments, supports 72, connected to the distal surface of the circumferential flange 70 and extending radially outward from the outer surface of the sidewall 40 of the scrubbing cap 32, may be provided around a circumference of the circumferential flange 70 to support and strengthen the circumferential flange 70.

In some embodiments, protrusions 96 may extend radially outward from the outer surface of the sidewall 40 of the scrubbing cap 32 to aid the user in gripping the scrubbing cap 32 during removal of the removable cover 64 and during the scrubbing of the needle-free connector 26.

The disinfecting cap 34 comprises an open proximal end 74, a closed distal end 76, and a sidewall 78 extending from the open proximal end 74 to the closed distal end 76. The sidewall 78, together with the closed distal end 76, define a chamber 80 sized and shaped to receive the needle-free connector 26 of the indwelling IV catheter. The disinfecting cap 34 may be substantially cylindrical or may be tapered in a proximal direction, such that an outer diameter of the sidewall 78 of the disinfecting cap 34 at the open proximal end 74 of the disinfecting cap 34 is greater than an outer diameter of the disinfecting cap 34 at the closed distal end 76 of the disinfecting cap 34. A compressible sponge 82 saturated with disinfectant 46 is contained in the chamber 80 of the disinfecting cap 34. The sponge 82 may be substan-tially cylindrical and may fill at least a portion of the chamber 80 of the disinfecting cap 34.

In some embodiments, the sponge may be a porous sponge or may have at least one slit and/or at least one recess adapted to receive the needle-free connector 26 of the indwelling IV catheter when the needle-free connector 26 is inserted into the disinfecting cap 34.

In some embodiments, threads 84 may extend radially inward from the inner surface of the sidewall 78 of the disinfecting cap 34. After inserting the needle-free connector 26 into the chamber 80 of the disinfecting cap 34, the disinfecting cap 34 may be rotated with respect to the needle-free connector 26 to engage the threads 84 of the disinfecting cap 34 with threads or tabs 86 provided on the needle-free connector 26 to secure the disinfecting cap 34 onto the needle-free connector 26 and force the needle-free connector 26 into contact with the disinfectant saturated sponge 82 contained in the chamber 80 of the disinfecting cap 34.

The open proximal end 74 of the disinfecting cap 34 is sealed by a removable cover 88. The removable cover 88 may be a film that is adhered to the open proximal end 74 of the disinfecting cap 34. The removable cover 88 may include a pull tab 90 extending outwardly from a sealing portion 92 of the removable cover 88. In use, a medical practitioner can grasp the pull tab 90 to remove the remov-able cover 88 from the disinfecting cap 34. In some embodi-ments, a circumferential flange 94 may extend radially outward from the open proximal end 74 of the scrubbing cap 34, and the removable cover 88 may be adhered to the circumferential flange 94. In some embodiments, supports connected to the distal surface of the circumferential flange 94 and extending radially outward from the outer surface of the sidewall 78 of the disinfecting cap 34 may be provided around a circumference of the circumferential flange 94 to support and strengthen the circumferential flange 94.

In some embodiments, protrusions 96 may extend radially outward from the outer surface of the sidewall 78 of the disinfecting cap 34 to aid the user in gripping the disinfect-ing cap 34 during the removal of the removable cover 88 and during the insertion of the disinfecting cap 34 onto the needle-free connector 26.

A tip cap 98 adapted to connect to and cover the syringe tip 18 of the prefilled syringe 12 extends distally from the closed distal end 76 of the disinfecting cap 34 or the closed distal end 38 of the scrubbing cap 32.

The tip cap 98 may comprise a closed proximal end 100, an open distal end 102, and a sidewall 104 extending from the closed proximal end 100 to the open distal end 102. The sidewall 104 together with the closed proximal end 100 define a cavity 106 sized and shaped to receive and cover the syringe tip 18 of the syringe 12, and the sidewall 104 of the tip cap 98 may be provided with external threads 108 adapted to engage internal threads 110 of the luer lock 24 surrounding the syringe tip 18. Engagement of the tip cap 98 with the syringe 12 encases the syringe tip 18 in the tip cap 98, thereby keeping the syringe tip 18 sterile until it is used.

In one embodiment of the disinfecting assembly 10a (FIGS. 1-4), the tip cap 98 extends from the closed distal end 38 of the scrubbing cap 32, and the closed distal end 76 of the disinfecting cap 34 is removably bonded to the removable cover 64 of the scrubbing cap 32. The closed distal end 76 of the disinfecting cap 34 may be bonded to the removable cover 64 of the scrubbing cap 32 using any suitable bond that allows the disinfecting cap 34 to be removed from the removable cover 64 of the scrubbing cap 32 without removing the removable cover 64 of the disinfecting cap 34. Examples of such bonds include, but are not limited to, adhesive, glue, and an ultrasonically welded joint.

In some embodiments, the open proximal end 36 of the scrubbing cap 32 may include a retaining portion 112. The retaining portion 112 comprises a circumferential flange 114 extending radially outward from the open proximal end 36 of the scrubbing cap 32 and a retaining sidewall 116 extending proximally from an outer perimeter of the flange 114. The retaining sidewall 116 may include a recess 118 through which the pull tab 66 of the removable cover 64 of the scrubbing cap 32 extends. The closed distal end 76 of the disinfecting cap 34 is received in the retaining portion 112. The retaining portion 112 acts to reduce accidental removal of the disinfecting cap 34 from the scrubbing cap 32 prior to use.

In another embodiment of the disinfecting assembly 10c (FIGS. 6-8), the tip cap 98 extends from the closed distal end 38 of the scrubbing cap 32, and the disinfecting cap 34 is attached to the scrubbing cap 32 via a removable disc 120, and the open proximal end 36 of the scrubbing cap 32 may include the retaining portion 112. The retaining portion 112 comprises a circumferential flange 114 extending radially outward from the open proximal end 36 of the scrubbing cap 32 and a retaining sidewall 116 extending proximally from an outer perimeter of the circumferential flange 114. The retaining sidewall 116 may include the recess 118 through which the pull tab 66 of the removable cover 64 of the scrubbing cap 32 extends. The closed distal end 76 of the disinfecting cap 34 is received in the retaining portion 112. The disc 120 rests on the circumferential flange 114 of the retaining portion 112 and is held in place by a retention flange 122 extending radially inward around at least a portion of the open proximal end 36 of the retaining sidewall 116, such that the disc 120 is in a snap-fit engagement with the scrubbing cap 32.

A circumferential groove 124 is provided in the outer surface of the sidewall 78 of the disinfecting cap 34 at the closed distal end 76 of the disinfecting cap 34. A flexible, annular protrusion 126 extends proximally from the disc 120. The annular protrusion 126 is received in the circumferential groove 124 in a snap-fit engagement. While the circumferential groove 124 and the annular protrusion 126 are shown to be continuous, the circumferential groove 124 and/or the annular protrusion 126 may be segmented.

When using these embodiments (FIGS. 4 and 8), the disinfecting cap 34 and the disc 120, if provided, are disconnected from the scrubbing cap 32 and set to the side. The removable cover 64 is then removed from the scrubbing cap 32, and the needle-free connector 26 of the indwelling IV catheter is inserted into the chamber 42 of the scrubbing cap 32 and moved longitudinally and/or rotated with respect to the scrubber 44 to scrub the needle-free connector 26 and clean the needle-free connector 26 with the disinfectant 46. The scrubbing cap 32 is then disconnected from the prefilled syringe 12. The prefilled syringe 12 is connected to the needle-free connector 26, and the needle-free connector 26 and the indwelling IV catheter are flushed with fluid from the syringe 12. The syringe 12 is disconnected from the needle-free connector 26. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. A medicinal fluid is injected into the indwelling IV catheter or blood is drawn through the indwelling IV catheter. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The prefilled syringe 12 or another prefilled syringe is connected to the needle-free connector 26, and the needle-free connector 26 and the indwelling IV catheter are flushed with fluid from the syringe 12. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The indwelling IV catheter may then be locked using a lock syringe. The removable cover 88 is then removed from the disinfecting cap 34, and the disinfecting cap 34 is attached to the needle-free connector 26.

In another embodiment of the disinfecting assembly 10b (FIG. 5), the tip cap 98 extends from the closed distal end 76 of the disinfecting cap 34 and the closed distal end 38 of the scrubbing cap 32 is removably bonded to the removable cover 88 of the disinfecting cap 34. The closed distal end 38 of the scrubbing cap 32 may be bonded to the removable cover 88 of the disinfecting cap 34 using any suitable bond that allows the scrubbing cap 32 to be removed from the removable cover 88 of the disinfecting cap 34 without removing the removable cover 88 of the scrubbing cap 32. Examples of such bonds include, but are not limited to, adhesive, glue, and ultrasonically welded joint.

In some embodiments, the open proximal end 74 of the disinfecting cap 34 may include a retaining portion 112. The retaining portion 112 comprises a circumferential flange 114 extending radially outward from the open proximal end 74 of the disinfecting cap 34, and a retaining sidewall 116 extending distally from an outer perimeter of the circumferential flange 114. The retaining sidewall 116 may include a recess 118 through which the pull tab 90 of the removable cover 88 of the disinfecting cap 34 extends. The closed distal end 38 of the scrubbing cap 32 is received in the retaining portion 112. The retaining portion 112 acts to reduce accidental removal if the scrubbing cap 32 from the disinfecting cap 34 prior to use.

Alternatively (FIG. 9, disinfecting assembly 10d), the scrubbing cap 32 is attached to the disinfecting cap 34 via a removable disc 120 and the open proximal end 74 of the disinfecting cap 34 may include a retaining portion 112. The retaining portion 112 comprises a circumferential flange 114 extending radially outward from the open proximal end 74 of the disinfecting cap 34, and a retaining sidewall 116 extending distally from an outer perimeter of the circumferential flange 114. The retaining sidewall 116 may include a recess 118 through which the pull tab 90 of the removable cover 88 of the disinfecting cap 34 extends. The closed distal end 38 of the scrubbing cap 32 is received in the retaining portion 112. The disc 120 rests on the circumferential flange 114 of the retaining portion 112 and is held in place by a retention flange 122 extending radially inward around at least a portion of the proximal end of the retaining sidewall 116, such that the disc 120 is in a snap-fit engagement with the disinfecting cap 34.

When using these embodiments, the scrubbing cap 32 and the disc 120, if provided, are disconnected from the disinfecting cap 34. The removable cover 64 is then removed from the scrubbing cap 32 and the needle-free connector 26 of the indwelling IV catheter is inserted into the chamber 42 of the scrubbing cap 32 and moved longitudinally and/or rotated with respect to the scrubber 44 to scrub the needle-free connector 26 and clean the needle-free connector 26 with the disinfectant 46. The disinfecting cap 34 is then disconnected from the prefilled syringe 12 and set aside. The prefilled syringe 12 is connected to the needle-free connector 26 and the needle-free connector 26 and the indwelling IV catheter are flushed with fluid from the syringe 12. The syringe 12 is disconnected from the needle-free connector 26. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. A medicinal fluid is injected into the indwelling IV catheter or blood is drawn through the indwelling IV catheter. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The prefilled syringe 12 or another prefilled syringe is connected to the needle-free connector 26, and the needle-free connector 26 and the indwelling IV catheter are flushed with fluid from the syringe 12. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The removable cover 88 is then removed from the disinfecting cap 34 and the disinfecting cap 34 is attached to the needle-free connector 26.

In other embodiments (FIGS. 10-18), the scrubbing cap 32 and the disinfecting cap 34 are connected to one another and to the prefilled syringe 12 by a housing 128. The housing 128 comprises an open proximal end 130, a closed distal end 132, and a sidewall 134 extending from the open proximal end 130 to the closed distal end 132. The sidewall 134 together with the closed distal end 132 define a cavity 136 sized and shaped to receive the disinfecting cap 34 and at least a portion of the scrubbing cap 32.

The tip cap 98 adapted to connect to and cover the syringe tip 18 of the prefilled syringe 12 extends distally from the closed distal end 132 of the housing 128.

In one embodiment, the tip cap 98 for connecting to and covering the syringe tip 18 extends distally from the closed distal end 132 of the housing 128. The tip cap 98 may comprise a closed proximal end 100, an open distal end 102, and a sidewall 104 extending from the closed proximal end 100 to the open distal end 102. The sidewall 104 together with the closed proximal end 100 define a cavity 106 sized and shaped to receive and cover the syringe tip 18 of the syringe 12, and the sidewall 104 of the tip cap 98 may be provided with external threads 108 adapted to engage the internal threads 110 of a luer lock 24 surrounding the syringe tip 12. Engagement of the tip cap 98 with the syringe 12 encases the syringe tip 18 in the tip cap 98, thereby keeping the syringe tip 18 sterile until it is used.

The housing 128 may comprise a body portion 138 and a retaining portion 140. An inner diameter of the retaining portion 140 may be greater than an inner diameter of the body portion 138 creating a circumferential flange 142 that extends radially inward into the cavity 136 of the housing 128. The outer diameter of the retaining portion 140 of the housing 128 may also be greater than the outer diameter of the body portion 138 of the housing 128. The sidewall 134 of the housing 128 may include a recess 144 through which the pull tab 90 of the removable cover 88 of the disinfecting cap 34 extends. The recess 144 may be provided in the retaining portion 140 of the housing 128.

In a first embodiment of the disinfecting assembly 10e with a housing 128 (FIGS. 10-13), the disinfecting cap 34 is positioned in the cavity 136 of the housing 128, such that the closed distal end 76 of the disinfecting cap 34 rests on the closed distal end 132 of the housing 128. A flexible, annular protrusion 146 extends radially inward from an inner surface of the sidewall 134 of the housing 128 in the retaining portion 140 of the housing 128. The annular protrusion 146 is proximal to the open proximal end 74 of the disinfecting cap 34. A circumferential groove 148 is provided in the outer surface of the sidewall 40 of the scrubbing cap 32. While the circumferential groove 148 is shown to be continuous and the annular protrusion 146 is shown to be segmented, the circumferential groove 148 and/or the annular protrusion 146 may be segmented or continuous. The closed distal end 38 of the scrubbing cap 32 is received in the cavity 136 of the housing 128 with the annular protrusion 146 of the housing 128 removably received in the circumferential groove 148 of the scrubbing cap 32 in a snap-fit engagement, the closed distal end 38 of the scrubbing cap 32 adjacent the open proximal end 74 of the disinfecting cap 34, and the open proximal end 36 of the scrubbing cap 32 extending proximally from the housing 128.

Alternatively, the annular protrusion 146 may be provided on the outer surface of the sidewall 40 of the scrubbing cap 32, and the circumferential groove 148 may be provided in an inner surface of the sidewall 134 of the housing 128 in the retaining portion 140 of the housing 128.

In a second embodiment of the disinfecting assembly 10g with a housing 128 (FIGS. 15-17), the disinfecting cap 34 is positioned in the cavity 136 of the housing 128, such that the closed distal end 74 of the disinfecting cap 34 rests on the closed distal end 132 of the housing 128. Threads 150 are provided on the inner surface of the sidewall 134 of the retaining portion 140 of the housing 128. A circumferential attachment flange 152 extends proximally from an outer surface of the sidewall 40 of the scrubbing cap 32. Threads 154 are provided on an outer surface of the attachment flange 152. The threads 150 on the inner surface of the retaining portion 140 of the housing 128 engage the threads 154 on the outer surface of the attachment flange 152 of the scrubbing cap 32 to attach the scrubbing cap 32 to the housing 128. A height in the longitudinal direction of the attachment flange 152 containing the threads 154 may be substantially equal to a height in the longitudinal direction of the retaining portion 140 of the housing 128. The closed distal end 38 of the scrubbing cap 32 is received in the cavity 136 of the housing 128 with the threads 150 on the inner surface of the retaining portion 140 of the housing 128 engaging the threads 154 on the outer surface of the attachment flange 152 of the scrubbing cap 32, the closed distal end 38 of the scrubbing cap 32 adjacent the open proximal end 74 of the disinfecting cap 34, and the open proximal end 36 of the scrubbing cap 32 extending proximally from the housing 128.

When using these embodiments (FIGS. 13 and 17), the scrubbing cap 32 is disconnected from the housing 128. The removable cover 64 is then removed from the scrubbing cap 32, and the needle-free connector 26 is inserted into the chamber 42 of the scrubbing cap 32 and moved longitudinally and/or rotated with respect to the scrubber 44 to scrub the needle-free connector 26 and clean the needle-free connector 26 with the disinfectant 46. The housing 128 is then disconnected from the prefilled syringe 12. The prefilled syringe 12 is connected to the needle-free connector 26, and the needle-free connector 26 and the indwelling IV catheter are flushed with fluid from the syringe 12. The syringe 12 is disconnected from the needle-free connector 26. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. A medicinal fluid is injected into the indwelling IV catheter or blood is drawn through the indwelling IV catheter. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The prefilled syringe 12 or another prefilled syringe is connected to the needle-free connector 26, and the needle-free connector 26 and the indwelling IV catheter are flushed with fluid from the syringe 12. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The indwelling IV catheter may then be locked using a lock syringe. The disinfecting cap 34 is removed from the housing 128, the removable cover 88 is removed from the disinfecting cap 34, and the disinfecting cap 34 is attached to the needle-free connector 26.

In a third embodiment of a disinfecting assembly 10f with a housing 128 (FIG. 14), the scrubbing cap 32 is positioned in the cavity 136 of the housing 128, such that the closed distal end 38 of the scrubbing cap 32 rests on the closed distal end 132 of the housing 128. A flexible, annular protrusion 146 extends radially inward from an inner surface of the sidewall 134 of the housing 128 in the retaining portion 140 of the housing 128. The annular protrusion 146 is proximal to the open proximal end 36 of the scrubbing cap 32. A circumferential groove 148 is provided in the outer surface of the sidewall 78 of the disinfecting cap 34. The circumferential groove 148 and/or the annular protrusion 146 may be segmented or continuous. The closed distal end 76 of the disinfecting cap 34 is received in the cavity 136 of the housing 128 with the annular protrusion 146 of the housing 128 removably received in the circumferential groove 148 of the disinfecting cap 34 in a snap-fit engagement, the closed distal end 76 of the disinfecting cap 34 adjacent the open proximal end 36 of the scrubbing cap 32, and the open proximal end 74 of the disinfecting cap 34 extending proximally from the housing 128.

Alternatively, the annular protrusion 146 may be provided on the outer surface of the sidewall 40 of the disinfecting cap 34, and the circumferential groove 148 may be provided in an inner surface of the sidewall 134 of the housing 128 in the retaining portion 140 of the housing 128

In a fourth embodiment of a disinfecting assembly 10h with a housing 128 (FIG. 18), the scrubbing cap 32 is positioned in the cavity 136 of the housing 128, such that the closed distal end 38 of the scrubbing cap 32 rests on the closed distal end 132 of the housing 128. Threads 150 are provided on the inner surface of the sidewall 132 of the retaining portion 140 of the housing 128. A circumferential attachment flange 152 extends proximally from an outer surface of the sidewall 78 of the disinfecting cap 34. Threads 154 are provided on an outer surface of the attachment flange 152. The threads 150 on the inner surface of the retaining portion 140 of the housing 128 engage the threads 154 on the outer surface of the attachment flange 152 of the disinfecting cap 34 to attach the disinfecting cap 34 to the housing 128. A height in the longitudinal direction of the attachment flange 152 containing the threads 154 may be substantially equal to a height in the longitudinal direction of the retaining portion 140 of the housing 128. The closed distal end 76 of the disinfecting cap 34 is received in the cavity 136 of the housing 128 with the threads 150 on the inner surface of the retaining portion 140 of the housing 128 engaging the threads 154 on the outer surface of the attachment flange 152 of the disinfecting cap 34, the closed distal end 74 of the disinfecting cap 34 adjacent the open proximal end 36 of the scrubbing cap 32, and the open proximal end 76 of the disinfecting cap 34 extending proximally from the housing 128.

When using these embodiments, the disinfecting cap 34 is disconnected from the housing 128 and set aside. The removable cover 64 is then removed from the scrubbing cap 34, and the needle-free connector 26 is inserted into the chamber 42 of the scrubbing cap 32 and moved longitudinally and/or rotated with respect to the scrubber 44 to scrub the needle-free connector 26 and clean the needle-free connector 26 with the disinfectant 46. The housing 128 is then disconnected from the prefilled syringe 12. The prefilled syringe 12 is connected to the needle-free connector 26 and the needle-free connector 26 and the indwelling IV catheter are flushed with fluid from the syringe 12. The syringe 12 is disconnected from the needle-free connector 26. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. A medicinal fluid is injected into the indwelling IV catheter or blood is drawn through the indwelling IV catheter. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The prefilled syringe 12 or another prefilled syringe is connected to the needle-free connector 26, and the needle-free connector 26 and the indwelling IV catheter are flushed with fluid from the syringe 12. The needle-free connector 26 may again be inserted into the chamber 42 of the scrubbing cap 32 and moved longitudinally and/or rotated with respect to the scrubber 44 to scrub the needle-free connector 26 and clean the needle-free connector 26 with the disinfectant 46. The indwelling IV catheter may then be locked using a lock syringe. The disinfecting cap 34 is removed from the housing 128, the removable cover 88 is removed from the disinfecting cap 34, and the disinfecting cap 34 is attached to the needle-free connector 26.

The use of caps for passive disinfection and maintaining a physical barrier over the needle-free connector of the indwelling IV catheter has been recommended by guidelines, including the INS 2021 Infusion Therapy Standards of Practice. Caps, being a relatively new concept in vascular care, are still gaining acceptance within clinical facilities and are often overlooked by medical practitioners. Integrating disinfecting caps and scrubbing caps with prefilled flushing syringes ensures easy access to disinfecting caps during indwelling IV catheter flushes and after a medication push or fluid withdrawal through the needle-free connector and the indwelling IV catheter.

The inventive disinfecting assembly, when coupled with a standard prefilled flushing syringe, provides all of the necessary components for proper cleaning and disinfecting of the needle-free connector and the indwelling IV catheter in a single device. The inventive disinfecting assembly can be directly implemented on existing prefilled syringes, such as the BD PosiFlush™ syringe. No modifications of the existing prefilled syringe are required, as the inventive disinfecting assembly can be directly threaded onto the syringe tip and luer lock of the prefilled flushing syringe in lieu of a tip cover.

Whereas particular aspects of this invention have been described above for purposes of illustration, it will be evident to those skilled in the art that numerous variations of the details of the present invention may be made without departing from the invention.

The invention claimed is:

1. A disinfecting assembly for a prefilled flushing syringe, the disinfecting assembly comprising:
  a scrubbing cap comprising:
    an open proximal end, a closed distal end, and a sidewall extending from the open proximal end of the scrubbing cap to the closed distal end of the scrubbing cap,
    a chamber defined by the sidewall of the scrubbing cap together with the closed distal end of the scrubbing cap and sized and shaped to receive a needle-free connector of an intravenous (IV) catheter,
    a scrubber and a disinfectant contained within the chamber of the scrubbing cap, and
    a first removable cover sealing the open proximal end of the scrubbing cap; and comprising:
  a disinfecting cap connected to the scrubbing cap and configured to be removed from the scrubbing cap without removing the first removable cover, the disinfecting cap comprising:
    an open proximal end, a closed distal end, and a sidewall extending from the open proximal end of the disinfecting cap to the closed distal end of the disinfecting cap,
    a chamber defined by the sidewall of the disinfecting cap together with the closed distal end of the disinfecting cap and sized and shaped to receive a needle-free connector of an intravenous catheter, and
    a compressible sponge and a disinfectant contained within the chamber of the disinfecting cap.

2. The disinfecting assembly of claim 1, wherein the scrubber fills at least a portion of the chamber of the scrubbing cap.

3. The disinfecting assembly of claim 1, wherein the scrubber is saturated with the disinfectant and/or the scrubber is fastened in a proximal portion of the chamber of the scrubbing cap and the disinfectant is contained in a distal portion of the chamber of the scrubbing cap.

4. The disinfecting assembly of claim 3, wherein the scrubber is held in the proximal portion of the scrubbing cap by an interaction between a circumferential flange extending radially outward from the scrubber and a ledge extending radially inward from an inner surface of the sidewall of the scrubbing cap.

5. The disinfecting assembly of claim 1, wherein an outer diameter of a proximal portion of the scrubbing cap is greater than an outer diameter of a distal portion of the scrubbing cap, and/or an inner diameter of the proximal portion of the scrubbing cap is greater than an inner diameter of the distal portion of the scrubbing cap.

6. The disinfecting assembly of claim 5, wherein the scrubber is substantially contained in the proximal portion of the scrubbing cap.

7. The disinfecting assembly of claim 1, wherein the scrubber has at least one slit and/or at least one recess in the proximal end of the scrubber, and the at least one slit and/or the at least one recess are adapted to receive the needle-free connector of an intravenous catheter when the needle-free connector is inserted into the scrubbing cap.

8. The disinfecting assembly of claim 1, wherein the first removable cover is a film that is adhered to the open proximal end of the scrubbing cap.

9. The disinfecting assembly of claim 1, wherein the first removable cover includes a pull tab extending outwardly from a sealing portion of the first removable cover.

10. The disinfecting assembly of claim 1, wherein a circumferential flange extends radially outward from the open proximal end of the scrubbing cap, and the first removable cover is adhered to the circumferential flange.

11. The disinfecting assembly of claim 1, wherein the compressible sponge fills at least a portion of the cavity of the disinfecting cap.

12. The disinfecting assembly of claim 1, wherein threads are provided in an inner surface of the sidewall of the disinfecting cap.

13. The disinfecting assembly of claim 1, wherein the open proximal end of the disinfecting cap is sealed by a second removable cover.

14. The disinfecting assembly of claim 13, wherein the second removable cover is a film that is adhered to the open proximal end of the disinfecting cap.

15. The disinfecting assembly of claim 13, wherein the second removable cover includes a pull tab extending outwardly from a sealing portion of the second removable cover.

16. The disinfecting assembly of claim 13, wherein a circumferential flange extends radially outward from the open proximal end of the disinfecting cap, and the second removable cover is adhered to the circumferential flange.

17. The disinfecting assembly of claim 1, wherein protrusions extend radially outward from an outer surface of the sidewall of the scrubbing cap to aid a user in gripping the scrubbing cap during removal of a first removable cover and during the scrubbing of the needle-free connector and/or protrusions extend radially outward from an outer surface of the sidewall of the disinfecting cap to aid the user in gripping the disinfecting cap during removal of the second removable cover and during placement of the disinfecting cap on the needle-free connector.

18. The disinfecting assembly of claim 1, further comprising a tip cap extending distally from the closed distal end of one of the disinfecting cap and the scrubbing cap and adapted to connect to and cover a syringe tip of the prefilled flushing syringe.

19. The disinfecting assembly of claim 18, wherein the tip cap comprises a closed proximal end, an open distal end, and a sidewall extending from the closed proximal end to the open distal end, and the sidewall of the tip cap together with the closed proximal end of the tip cap define a cavity sized and shaped to receive and cover a syringe tip of the flushing syringe.

20. The disinfecting assembly of claim 1, wherein the disinfecting cap is connected to the scrubbing cap by a snap fitting.

21. The disinfecting assembly of claim 1, further comprising a removable disc configured to attach the disinfecting cap to the first removable cover.

22. A disinfecting assembly for a prefilled flushing syringe, the disinfecting assembly comprising:

a scrubbing cap comprising:

an open proximal end, a closed distal end, and a sidewall extending from the open proximal end of the scrubbing cap to the closed distal end of the scrubbing cap, a chamber defined by the sidewall of the scrubbing cap together with the closed distal end of the scrubbing cap and sized and shaped to receive a needle-free connector of an intravenous (IV) catheter, a scrubber and a disinfectant contained within the chamber of the scrubbing cap, and a scrubbing cap circumferential flange extending radially outward from the open proximal end of the scrubbing cap and a retaining sidewall extending proximally from an outer perimeter of the scrubbing cap circumferential flange, the retaining sidewall including a recess, and the open proximal end of the scrubbing cap including a retaining portion; and a first removable cover sealing the open proximal end of the scrubbing cap; and comprising:

a disinfecting cap connected to the scrubbing cap and configured to be removed from the scrubbing cap without removing the first removable cover, the disinfecting cap comprising:

an open proximal end, a closed distal end, and a sidewall extending from the open proximal end of the disinfecting cap to the closed distal end of the disinfecting cap, a chamber defined by the sidewall of the disinfecting cap together with the closed distal end of the disinfecting cap and sized and shaped to receive a needle-free connector of an intravenous catheter, a compressible sponge and a disinfectant contained within the chamber of the disinfecting cap, and wherein the closed distal end of the disinfecting cap is configured to be received in the retaining portion.

23. The disinfecting assembly of claim 22, further comprising a removable disc configured to attach the disinfecting cap to the first removable cover and the removable disc is configured to rest on the scrubbing cap circumferential flange and to be held in place by a retention flange extending radially inward around at least a portion the retaining sidewall, such that the disc is in a snap-fit engagement with the scrubbing cap.

* * * * *